(12) United States Patent
Sacchi et al.

(10) Patent No.: US 6,841,170 B2
(45) Date of Patent: Jan. 11, 2005

(54) PROCESS FOR PREPARING AN AUTOLOGOUS PLATELET GEL AND MEMBRANE THEREOF

(75) Inventors: Maria Cristina Sacchi, Via O. Remotti, 4 - 15040 San Michele (Province of Alessandria) (IT); Marco Bellanda, Alessandria (IT)

(73) Assignee: Maria Cristina Sacchi, Alessandria (IT)

(*) Notice: Subject to any disclaimer, the term of this patent is extended or adjusted under 35 U.S.C. 154(b) by 442 days.

(21) Appl. No.: 10/129,827
(22) PCT Filed: Dec. 13, 2000
(86) PCT No.: PCT/EP00/12661
§ 371 (c)(1), (2), (4) Date: May 7, 2002
(87) PCT Pub. No.: WO01/43787
PCT Pub. Date: Jun. 21, 2001

(65) Prior Publication Data
US 2002/0172666 A1 Nov. 21, 2002

(30) Foreign Application Priority Data
Dec. 14, 2000 (IT) ........................................ AL990010 U

(51) Int. Cl.⁷ ............................................... A61K 35/14
(52) U.S. Cl. ........................................................ 424/532
(58) Field of Search .......................................... 424/532

(56) References Cited

U.S. PATENT DOCUMENTS 5,585,007 A 12/1996 Antanavich et al. ......... 210/782
5,733,545 A * 3/1998 Hood, III ................. 424/93.72

FOREIGN PATENT DOCUMENTS

WO WO9627397 9/1996 .......... A61L/25/00
WO WO9811925 3/1998 .......... A61L/25/00

OTHER PUBLICATIONS

Che Ming Teng, "Comparison of the Platelet Aggregation Induced by Three Thrombin–Like Enzymes of Snake Venoms and Thrombin", *Thrombosis and Haemostasis*, O.F.K. Schattauer Verlagagesellschaft mbH Stuttgart 59 (2) 304–309, (1988).

Sachiyo et al., "Purification and Characterization of Bothrombin, a Fibrinogen–Clotting Serine Protease from the Venom of Bothrope Juraracs", Div. Biomed. Polymer Sci., Inst. Comprehensive Med., Sci, Fujita Health University, Toyoake, Aichi 470–11, Biochemistry, vol. 33, No. 7, pp. 1843–1849 (1994). (Abstract of article only).

* cited by examiner

Primary Examiner—Jean C. Witz
(74) Attorney, Agent, or Firm—Abelman, Frayne & Schwab

(57) ABSTRACT

A process is disclosed for preparing an autologous platelet gel and membranes thereof comprising mixing a platelet concentrate with a calcium salt and batroxobin. This process encompassing the use of batroxobin as the gel activator allows to overcome the prior art processes drawbacks connected with the use for the same purpose of human of bovine thrombin. A kit is also described for carrying out this process.

8 Claims, 2 Drawing Sheets

PROCESS FOR PREPARING AN AUTOLOGOUS PLATELET GEL AND MEMBRANE THEREOF

FIELD OF THE INVENTION

The present invention relates to a process for preparing an autologous platelet gel and membranes thereof, and a kit for carrying out this process.

BACKGROUND OF THE INVENTION

Marx and colleagues have shown that the use of platelet concentrate represents an innovative method to modulate and accelerate wound healing process, as well as bone regenerative processes (Oral surg., Oral Med., Oral Path 1998, 85: 638–646). Therefore these authors elaborated a technique allowing to isolate and precipitate platelets thereby obtaining an autologous platelet concentrate, which is neither toxic nor immunoreactive. This substance is able to enhance the effects of growth factors contained in platelets granules and which are initiators of metabolic pathway involved in wound healing steps.

According to Marx's protocol encompassing the use of a cellular separator, the platelet concentrate is prepared by carrying out a venous blood sample of 500 ml, namely an operation which is accomplished by means a venous catheter. The platelet concentrate is subsequently activated with calcium chloride and bovine thrombin to produce a platelet gel which can be combined with either autologous spongy and cortical bone or bone matrix consisting of bio-glasses.

In Italy Marx technique for the activation of a platelet gel cannot be carried out since bovine thrombin is no longer available on the market. In addition this method involving the use of very high amounts of blood requiring specific instrumentation and skilled personnel for preparing platelet concentrate, cannot be realised in a medical surgery so as to allow a routine use of the platelet gel.

In U.S. Pat. No. 5,585,007 and WO 98/11925 methods for preparing platelet gel are disclosed. These methods, although representing an improvement if compared to Marx's protocol, as they necessitate much lower blood amounts (50–60 ml), they require for platelet gel formation the use of bovine or human thrombin.

To date human thrombin can only be prepared by DNA recombinant technique. In Italy substances prepared according to this technique can be used only for in vitro experiments, but not for in vivo experiments.

Technical Problem

The need was felt of a process for preparing a platelet gel not presenting the prior art processes drawbacks, connected with the use as the activator of human or bovine thrombin.

SUMMARY OF THE INVENTION

The Applicant has unexpectedly found that it is possible to overcome the aforementioned drawback, by using as the activator batroxobin in place of thrombin.

The present invention therefore relates to a process for preparing a platelet gel comprising mixing a platelet concentrate with an inorganic or organic calcium salt and batroxobin.

A further object of the present invention relates to a kit for carrying out the process according to the present invention which in particular comprises:

a) a monouse sterile capsule of transparent plastic or glass material, fitted with a screw cap constituted in the upper part by a perforable membrane coated with a suitable sterile coating, said perforable membrane allowing the insertion of the needle of a syringe containing the platelet concentrate, and contemporaneously avoiding the air contact with the inside of the capsule, b) two plug injectors surmounting said perforable membrane containing respectively the calcium salt and batroxobin.

Finally further objects of the present invention are:

the autologous platelet gel obtained with the process according to the present invention.

a membrane comprising the autologous platelet gel according to the present invention.

Figure 1:
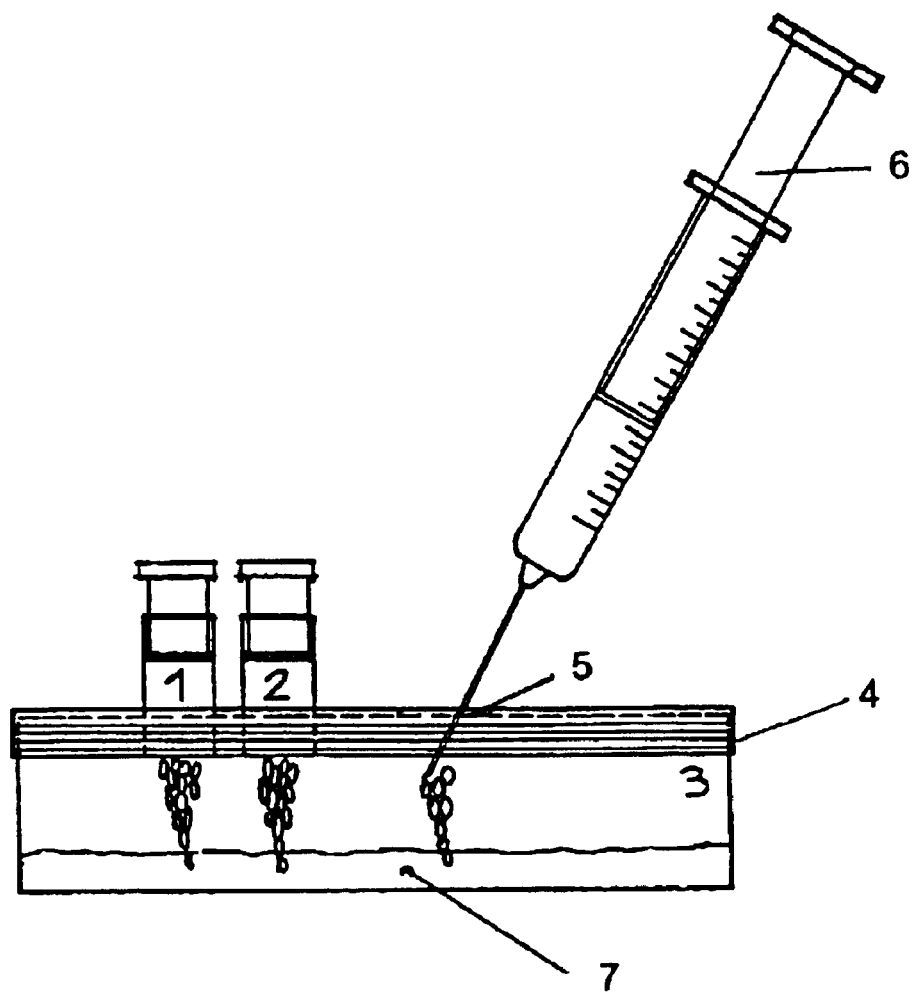
FIGS. 1 and 2 represent two preferred embodiments of the kit according to the present invention.

In particular in these figures: (3) represents the sterile monouse capsule, (4) the screw cap constituted in the upper part by a perforable membrane (5). (1) and (2) represent the two plug injectors surmounting said perforable membrane (5). Finally (6) represents the syringe containing the platelet concentrate, and (7) platelet gel formed during the reaction.

DETAILED DESCRIPTION OF THE INVENTION

1. Preferred Operating Conditions of the Process According to the Present Invention Preferably the inorganic calcium salt used in the process according to the present invention is calcium chloride, whereas when an organic calcium salt is sued this is preferably calcium gluconate. According to a particularly preferred embodiment, the process is carried out by using calcium gluconate.

The inorganic or organic calcium salt is in the form of an aqueous solution containing it in amounts ranging from $5.10^{-5}$ to 0.5 M.

According to a preferred embodiment in the process of the present invention, $8.10^{-5}$ M (80 $\mu$M) calcium chloride is utilised.

A more preferred embodiment foresees the use of 0,23 M calcium gluconate. The batroxobin used is preferably in the form of an aqueous solution having 1 thrombin international unit and is sold under the commercial name Botropase by Ravizza Farmaceutici S.p.A.

2. Method for Preparing the Platelet Concentrate

The platelet concentrate used in the process according to the present invention is prepared from whole blood (sample of 40–50 ml of venous blood), collected in 20 ml syringes, containing 4 ml sodium citrate used as anticoagulant ), by a two phases centrifugation, thereby obtaining an intermediate product being platelet rich plasma. This method allows to recover at least 80% of platelets present in whole blood.

In particular this technique encompasses the following steps. Venous blood is collected in 4 tubes and centrifuged at 180 g for 20 minutes. After this treatment two phases are obtained a dark one constituted by precipitated red and white cells at the bottom of the tubes, and a clear one visible in the upper part of the probe, consisting of platelet rich plasma. This plasma is taken and transferred by means of a Pasteur pipette into other 4 tubes and centrifuged at 580 g for 20 minutes. Thanks to this faster centrifugation (580 g versus 180 g) it is possible to obtain platelets sedimentation as a dense small bottom said "pellet". The liquid supernatant consists of platelet poor plasma.

The tubes are emptied, however leaving in each of them a small aliquot (1.5 ml) of platelet poor plasma necessary to suspend once again the "pellet" thereby obtaining a homogeneous suspension.

Thus proceeding it is possible to obtain a final platelet concentrate (of about 6 ml) deriving from the unification of the platelets suspensions present in the 4 tubes. This platelet concentrate after a rest period of about 15 minutes at room temperature, is ready to be used as reactant in the process according to the present invention.

3. Membranes According to the Present Invention and Method for Preparing Them

The membrane according to the present invention may contain active principles such as antibacterial agents, disinfectants, and/or sterile excipients etc.

Preferably the membrane according to the present invention essentially consists of the autologous platelet gel according to the present invention.

These membranes are obtained by simply eliminating the liquid in excess.

For example if the platelet gel preparation occurs in plastic or glass Petri dishes (like those utilised in cellular cultures), it is possible to obtain a thin membrane, as the gel during the activation takes the form of the container.

In this case by eliminating the liquid in excess by means for example of a Pasteur pipette released during the gel formation it is possible to obtain a pliable membrane having a well defined contour.

The removed liquid in excess consisting of batroxobin and calcium salt is added to the platelet poor plasma coming from the second centrifugation and determines after 20–30 minutes the formation of a further thick platelet gel.

4. The Kit According to the Present Invention

Figure 2:
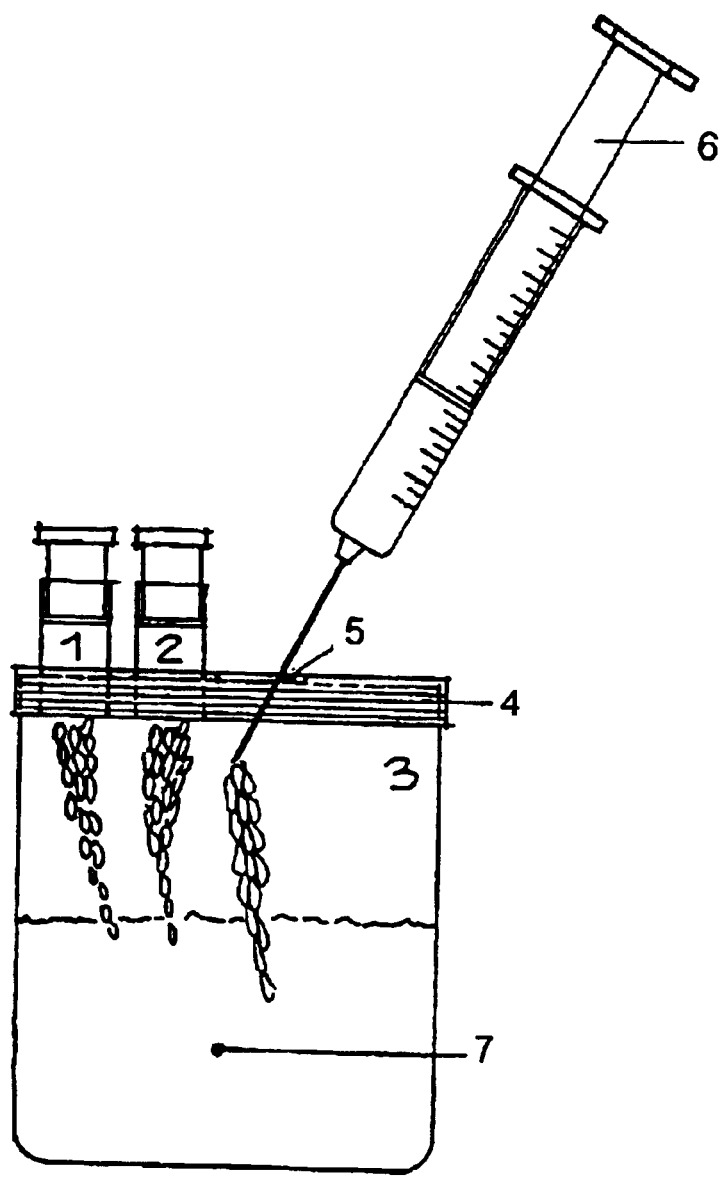

FIGS. 1 and 2 represent preferred embodiment of the kit according to the present invention.

In particular in these figures: (3) represents the sterile monouse capsule, (4) the screw cap constituted in the upper part by a perforable membrane (5). This membrane is coated with a sterile coating normally used in phamaceutical and diagnositc industry such as aluminum film or another equivalent material. (1) and (2) represent the two plug injectors surmounting said perforable membrane (5) and containing respectively the inorganic or organic calcium salt (more preferably 0.23 M calcium gluconate), and batroxobin. Finally (6) represents the syringe containing the platelet concentrate, and (7) platelet gel formed during the reaction. A manual pressure onto the cap injector (1) allows the outlet of calcium gluconate in amounts of from 0.3 to 0.5 ml into the capsule (3). Analogously a manual pressure onto the cap injector (2) allows the outlet of batroxobin in amounts of from 0.3 to 0.5 ml. The capsule (3) reported in FIG. 1 has preferably a capacity of from 10 to 20 ml, whereas the same capsule of the kit reported in FIG. 2 permits to obtain membranes of diameter of from 3 to 9 cm as the capsule may have a diameter ranging from 3.5 to 10.0 cm.

The process according to the present invention carried out with the aforementioned kit encompasses the following steps:

A) charging a 10 ml syringe (6) with a platelet concentrate amount ranging from 3 to 9 ml;

B) removing the sterile coating from the perforable membrane (5) and introducing the needle of the syringe into the capsule (3) through the perforable membrane (5);

C) pressing in rapid succession the cap injectors (1) and (2) containing respectively the calcium gluconate and batroxobin and the piston of the syringe (6) inside the capsule (3);

D) gently stirring with a rotating movement for about 30 seconds the capsule (3)

E) unscrewing the screw cap (4), and taking the platelet gel (7) thus formed.

What is claimed is:

1. A process for preparing a platelet gel comprising mixing a platelet concentrate with calcium chloride and batroxobin, wherein said platelet concentrate is obtained with a process comprising:

i) centrifuging 40–50 ml of venous blood at 180 g for 20 minutes thereby obtaining two phases a dark one constituted by precipitated red and white cells at the bottom of the centrifuge probe, and a clear one visible in the upper part of the same tube, consisting of platelet rich plasma;

ii) centrifuging the recovered platelet rich plasma at 580 g for 20 minutes thereby obtaining platelets sedimentation as "pellets" whereas the liquid supernatant consists of platelet poor plasma;

iii) suspending said pellets in an aliquot of said platelet poor plasma necessary to obtain a platelet concentrate of about 6 ml.

2. A process for preparing a platelet gel comprising mixing a platelet concentrate with an organic or inorganic calcium salt and batroxobin, wherein said platelet concentrate is obtained with a process comprising:

i) centrifuging 40–50 ml of venous blood at 180 g for 20 minutes thereby obtaining two phases a dark one constituted by precipitated red and white cells at the bottom of the centrifuge probe, and a clear one visible in the upper part of the same tube, consisting of platelet rich plasma;

ii) centrifuging the recovered platelet rich plasma at 580 g for 20 minutes thereby obtaining platelets sedimentation as "pellets" whereas the liquid supernatant consists of platelet poor plasma;

iii) suspending said pellets in an aliquot of said platelet poor plasma necessary to obtain a platelet concentrate of about 6 ml.

3. The process according to claim 2 wherein said organic salt is calcium gluconate.

4. The process according to claim 2 wherein the calcium salt is in the form of an aqueous solution containing it in an amount ranging from $5.10^{-5}$ to 0.5 M.

5. The process according to claim 4 wherein $8.10^{-5}$ M (80 $\mu$M) calcium chloride is utilised.

6. The process according to claim 4, wherein 0.23 M calcium gluconate is used.

7. The process according to claims 2, wherein batroxobin has 1 thrombin international unit/ml.

8. A process for preparing a platelet gel according to claim 2 carried out with a kit comprising:

a) a monouse sterile capsule (3) of transparent plastic or glass material, fitted with a screw cap (4) constituted in the upper part by a perforable membrane (5) coated with a suitable sterile coating removable at the moment of use, said perforable membrane (5) allowing the insertion of the needle of a syringe (6) containing said platelet concentrate, and contemporaneously avoiding the air contact with the inside of said capsule (3);

b) two plug injectors (1) and (2) surmounting said perforable membrane (5) containing respectively a calcium salt and batroxobin; said process comprising the following steps: with a screw cap (4) constituted in the upper part by a perforable membrane (5) coated with a suitable sterile coating removable at the moment of use, said perforable membrane (5) allowing the insertion of the needle of a syringe (6) containing said platelet concentrate, and contemporaneously avoiding the air contact with the inside of said capsule (3);

A) charging a 10 ml syringe (6) with a platelet concentrate amount ranging from 3 to 9 ml;

B) removing the sterile coating from the perforable membrane (5) and introducing the needle of the syringe (6) into the capsule (3) through the perforable membrane (5);

C) pressing in rapid succession the cap injectors (1) and (2) containing respectively 0.23 M of calcium gluconate in 0.3–0.5 ml of batroxobin having a concentration of 1 thrombin international unit/ml and the piston of the syringe (6) inside the capsule (3);

D) gently stirring with a rotating movement for about 30 seconds the capsule (3);

E) unscrewing the screw cap (4), and taking the platelet gel (7) thus formed, wherein the starting platelet concentrate is obtained with a process comprising:

i) centrifuging 40–50 ml of venous blood at 180 g for 20 minutes thereby obtaining two phases a dark one constituted by precipitated red and white cells at the bottom of the centrifuge probe, and a clear one visible in the upper part of the same tube, consisting of platelet rich plasma;

ii) centrifuging the recovered platelet rich plasma at 580 g for 20 minutes thereby obtaining platelets sedimentation as "pellets" whereas the liquid supernatant consists of platelet poor plasma;

iii) suspending said pellets in an aliquot of said platelet poor plasma necessary to obtain a platelet concentrate of about 6 ml.

* * * * *